(12) United States Patent  (10) Patent No.: US 8,394,335 B2
Greve  (45) Date of Patent: Mar. 12, 2013

(54) DRIVE TRAIN FOR AGITATION OF PRODUCTS IN BATCH RETORTS AND RELATED RETORT SYSTEM

(75) Inventor: Christopher G. Greve, Covington, LA (US)

(73) Assignee: Allpax Products LLC, Covington, LA (US)

( * ) Notice: Subject to any disclaimer, the term of this patent is extended or adjusted under 35 U.S.C. 154(b) by 381 days.

(21) Appl. No.: 12/718,324

(22) Filed: Mar. 5, 2010

(65) Prior Publication Data

US 2010/0272620 A1 Oct. 28, 2010

Related U.S. Application Data

(60) Provisional application No. 61/158,194, filed on Mar. 6, 2009.

(51) Int. Cl.
*A61L 2/04* (2006.01)
*A23L 3/00* (2006.01)

(52) U.S. Cl. .............. 422/307; 99/371; 99/359; 99/470; 366/144; 426/307

(58) Field of Classification Search .................... 99/371, 99/359; 426/405; 422/307; 366/144
See application file for complete search history.

(56) References Cited

U.S. PATENT DOCUMENTS

| 861,120 A | 3/1906 | Guibbini |
|---|---|---|
| 915,428 A | 3/1909 | Gubbini |
| 1,010,805 A | 12/1911 | Rogers |
| 1,491,031 A | 4/1924 | Chapman |
| 1,709,175 A | 4/1929 | Huygen |
| 1,975,073 A | 10/1934 | Chapman |
| 2,052,096 A | 8/1936 | Kronquest |
| 2,086,241 A | 7/1937 | Schaerr |
| 2,499,203 A | 2/1950 | Warren |
| 3,291,289 A | 12/1966 | Savage |
| 3,511,169 A | 5/1970 | Fritzberg et al. |
| 4,170,421 A | 10/1979 | Balding et al. |
| 4,348,912 A | 9/1982 | Thomas |
| 4,632,026 A | 12/1986 | Yamamoto et al. |
| 4,708,053 A | 11/1987 | Forsythe et al. |
| 4,748,816 A | 6/1988 | Arfert et al. |
| 4,929,087 A | 5/1990 | Brigolle |
| 5,626,824 A | 5/1997 | Ishikawa et al. |
| 5,836,204 A | 11/1998 | Skak |
| 5,857,312 A | 1/1999 | Walden |
| 6,605,252 B2 | 8/2003 | Omasa |
| 6,745,664 B2 | 6/2004 | Kopkie |
| 7,188,993 B1 | 3/2007 | Howe |
| 2003/0081499 A1 | 5/2003 | Friedman |
| 2007/0292570 A1 | 12/2007 | Walden et al. |

FOREIGN PATENT DOCUMENTS

| DE | 3628012 | 2/1988 |
|---|---|---|
| EP | 0512261 A | 4/1992 |
| EP | 1050366 A | 8/2000 |
| EP | 1151757 B | 11/2004 |

*Primary Examiner* — P. Kathryn Wright
(74) *Attorney, Agent, or Firm* — Thompson Hine LLP (57) ABSTRACT

A retort system includes a vessel defining a heating chamber and including a product receiving area therein, and a product agitating arm mounted for reciprocating movement through a wall of the vessel and having a first end within the vessel and a second end outside the vessel. A drive arrangement is located exterior of the vessel and operatively coupled to the arm for moving the arm in a reciprocating manner. The drive arrangement includes a crankshaft assembly, a first flywheel and a second flywheel. The crankshaft assembly includes a crank throw operatively coupled to the arm, the crankshaft assembly having a rotational axis offset from the crank throw. The first flywheel is mounted to the crankshaft assembly to a first side of the crank throw for rotation with the crankshaft assembly about the rotational axis. The second flywheel is mounted to the crankshaft assembly to a second side of the crank throw for rotation with the crankshaft assembly about the rotational axis.

9 Claims, 7 Drawing Sheets

DRIVE TRAIN FOR AGITATION OF PRODUCTS IN BATCH RETORTS AND RELATED RETORT SYSTEM

CROSS-REFERENCES

This application claims the benefit of U.S. Provisional Application Ser. No. 61/158,194, filed Mar. 6, 2009, the entirety of which is incorporated herein by reference.

TECHNICAL FIELD

The present application relates to sterilization autoclaves, commonly referred to as retorts, and, more particularly, to a drive train for an agitation-type retort in which containers within the retort vessel are moved in a reciprocating manner back and forth to enhance heat transfer to product within the containers.

BACKGROUND

In container sterilization of low acid shelf stable products, the products are commonly processed in batches using controlled autoclaves commonly know as retorts. Agitation of products in a retort promotes accelerated sterilization, shorter cool times and improved product quality due to reduction of the thermal burden to the product. Product within the retort is typically loaded into a retort basket, which may take the form of a welded metal crate that houses the product that is in individual containers. The containers are collated in a specific pattern in the retort basket, clamped tightly and loaded into the retort chamber. The entire basket is then clamped. In an agitation-type retort this basket clamp is mechanically connected to a rod that is reciprocated back and forth in order to move the basket, and thus the product containers, back and forth.

Previously, the energy required to agitate the load in a reciprocating motion was accomplished through a drive mechanism consisting of a crankshaft mounted directly to single unbalanced flywheel mounted directly to a motor driven gear reducer. The gear reducer had a given speed range that was controlled by a variable frequency drive to modulate the hertz output to the motor. On small loads ranging from 0 to 200 pounds, this method was successful in providing the required torque, speed, and stroke to achieve desired product agitation results.

It would be desirable to provide a drive mechanism suited for moving larger loads (e.g., weights ranging from 600-2000 pounds) at 0 to 2 g acceleration range.

SUMMARY

The present drive system provides a range of linear strokes of the containers in a retort, parallel to the retort shell or vessel length. A stroke is defined as the linear length that the product moves forward and then back to its starting position. A reciprocating mechanical connection rod or shaft is mounted to the retort basket and extends through an end wall of the retort. The reciprocating shaft extends out of the rear of the retort and is sealed through a packing gland mounted to the rear head of the vessel. The exterior end of the reciprocating shaft is linked to a connecting rod that in turn is linked to a crank throw structure of a crank shaft that also has associated spaced apart crank arm counterweights extending opposite the crank throw. Two rotary main shafts extend from opposite sides of the crank arm shaft and mounted to each shaft is, in one implementation, one of two counterbalanced flywheels, the counterbalance acting to offset the basket force. In another implementation the flywheels are balanced and it is the counterweight structure alone that acts to offset the basket force. The flywheels may be fixed to the respective shafts using a keyless shaft/hub locking device. The flywheels are driven by timing belts that connect to pulleys on an input drive shaft that is driven by a motor. The drive arrangement is, in one preferred configuration, mounted to a support structure that is separate from the retort vessel.

In one aspect, a retort system includes a vessel defining a heating chamber and including a product receiving area therein, and a product agitating arm mounted for reciprocating movement through a wall of the vessel and having a first end within the vessel and a second end outside the vessel. A drive arrangement is located exterior of the vessel and operatively coupled to the arm for moving the arm in a reciprocating manner. The drive arrangement includes a crankshaft assembly, a first flywheel and a second flywheel. The crankshaft assembly includes a crank throw operatively coupled to the arm, the crankshaft assembly having a rotational axis offset from the crank throw. The first flywheel is mounted to the crankshaft assembly to a first side of the crank throw for rotation with the crankshaft assembly about the rotational axis. The second flywheel is mounted to the crankshaft assembly to a second side of the crank throw for rotation with the crankshaft assembly about the rotational axis.

Utilization of the dual flywheels can dramatically reduce the motor horsepower required to accelerate and decelerate a weight load at a range 600-2000 lbs.

In one embodiment, a method of constructing the above retort system involves: determining a product load to be moved by operation of the drive arrangement; dependent upon the product load, defining a first weight for a first crank throw counterweight structure and a second weight for a second crank throw counterweight structure; providing a first crank throw counterweight to the first side of the crank throw and intermediate the crank throw and the first flywheel, the first crank throw counterweight having the first weight; and providing a second crank throw counterweight to the second side of the crank throw and intermediate the crank throw and the second flywheel, the second crank throw counterweight having the second weight.

In another aspect, a retort system includes a vessel defining a heating chamber and including a product receiving area therein, and a product agitating arm mounted for reciprocating movement through a wall of the vessel via a sealed bearing assembly mounted to the wall, the arm having a first end within the vessel and a second end outside the vessel. A drive arrangement is located exterior of the vessel and is operatively coupled to the arm for moving the arm in a reciprocating manner. The drive arrangement includes a first flywheel and a second flywheel spaced apart along a crankshaft that is operatively coupled to the arm at a crankshaft location between the first flywheel and the second flywheel. A support frame structure supports the drive arrangement and is independent of the vessel in order to limit stress applied to the vessel.

In a further aspect, a retort system includes a vessel defining a heating chamber and including a product receiving area therein, and a product agitating arm mounted for reciprocating movement through a wall of the vessel, the arm having a first end within the vessel and a second end outside the vessel. A drive arrangement is located exterior of the vessel and operatively coupled to the arm for moving the arm in a reciprocating manner. The drive arrangement includes a crankshaft operatively coupled to the arm via a crank throw of the crankshaft, a first crankshaft drive assembly positioned to drive the crankshaft from a first side of the crank throw and a second crankshaft drive assembly positioned to drive the crank shaft from a second side of the crank throw.

The balanced dual flywheel arrangement helps reduce the required torque needed to accelerate and decelerate the load compared to a conventional direct driven shaft and motor/gear reducer. The reduction in horsepower required with this type of drive train also offers energy savings due a significantly smaller motor requirement.

The details of one or more embodiments are set forth in the accompanying drawings and the description below. Other features, objects, and advantages will be apparent from the description and drawings, and from the claims.

DETAILED DESCRIPTION

Figure 1:
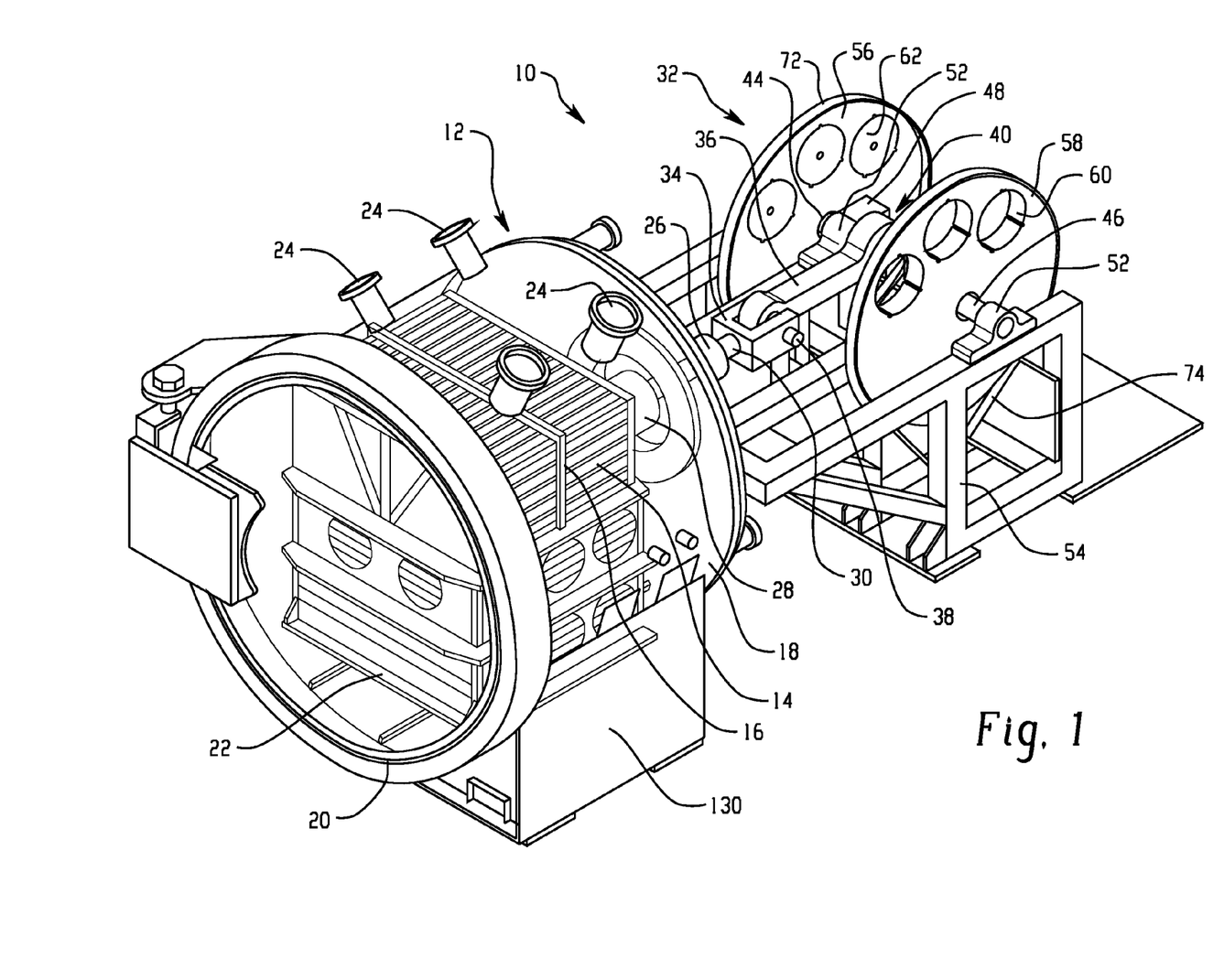
FIG. 1 is a perspective view of one embodiment of a retort system.

Referring to FIG. 1, one embodiment of a retort system 10 is shown. The retort system includes a retort system includes a vessel 12 defining a heating chamber. Product 14 is received in an area within the vessel. The product 14 may typically be loaded into a retort basket 16, which may take the form of a welded metal crate that houses the product that is in individual containers. The illustrated vessel includes a generally cylindrical wall 18 having its center axis extending generally horizontally. At one end of the cylindrical wall a pivotal access door 20 is provided for loading and removing product from the vessel. The product receiving area of the vessel includes product support structure 22 (e.g., rails and rollers) that enables the retort basket to be moved back and forth within the vessel in a direction parallel to the lengthwise axis of the vessel wall 18. The vessel wall may include inlet and outlet structures 24 for delivering hot fluid into and out of the vessel during heat treatment of food product. In this regard, the heating system provided for the vessel may be any one of the technologies commonly used in retort systems, such as heated water, heated air, steam or the like, or combinations of the same.

Figure 2:
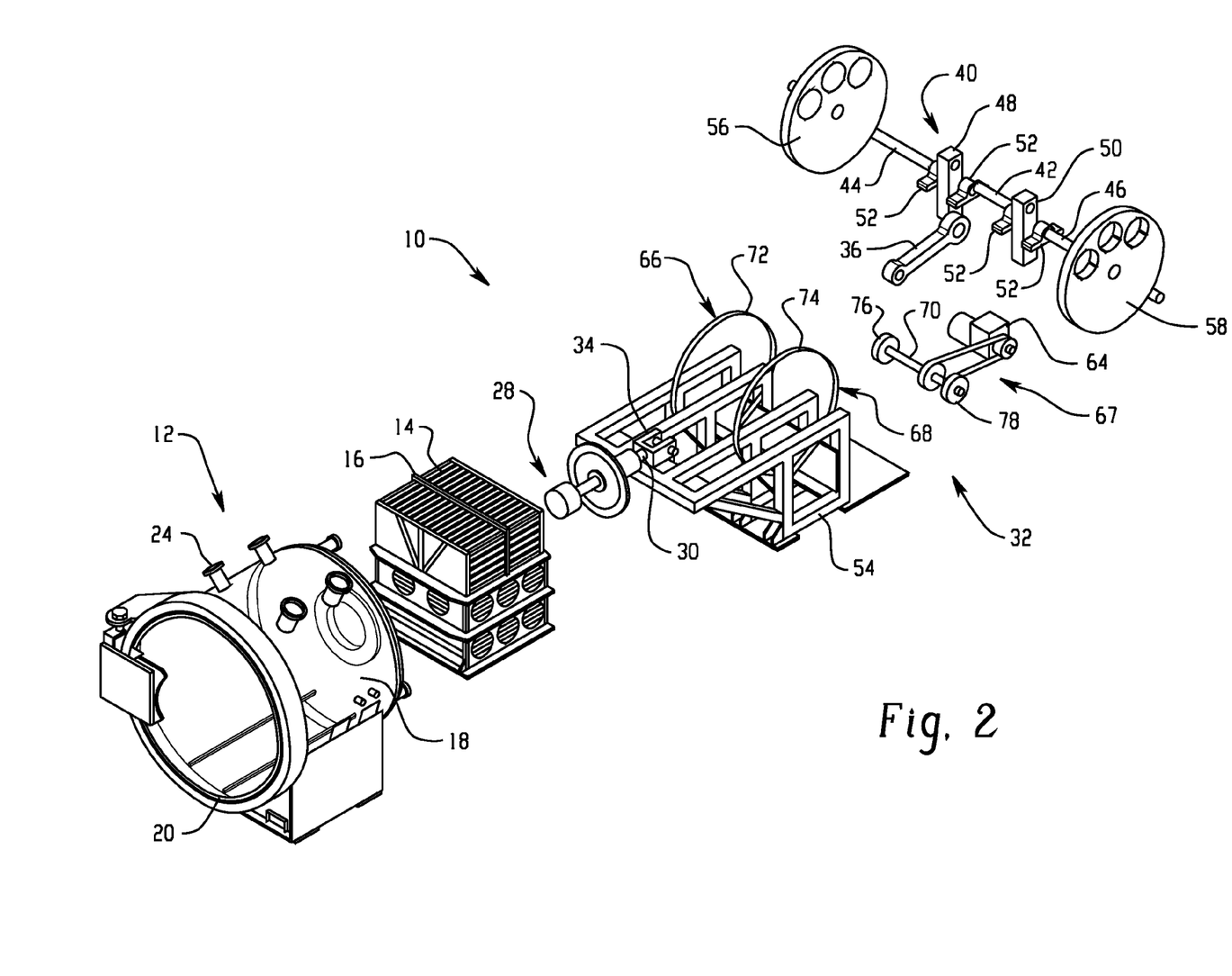
FIG. 2 is an exploded perspective of the retort system of FIG. 1.

A product agitating arm 26 is mounted for reciprocating movement through an end wall of the vessel and has an end 28 within the vessel and an end 30 outside the vessel. The internal end 28 of the arm is coupled to the retort basket to impart the reciprocating movement to the basket. A drive arrangement 32 is located exterior of the vessel and is operatively coupled to the arm 26 for moving the arm in a reciprocating manner. In the illustrated embodiment the arm end 30 is coupled to a female clevis 34 that is, in turn, pivotally connected one end of a connecting rod 36 via clevis pin 38. The opposite end of the connecting rod 36 is pivotally connected to a crank throw 42 of a crankshaft 40, where the rotational axis of the crankshaft is offset from the crank throw 42. In the illustrated embodiment the crankshaft is formed of multiple components including axially aligned main rotary shafts 44 and 46 that are rigidly connected to respective crank throw counterweights 48 and 50, which are in turn rigidly connected to a shaft forming the crank throw 42. Each of the main rotary shafts 44 and 46 is supported by a respective pair of spaced apart bearing blocks 52, which are mounted to a support frame 54. A flywheel 56 is rigidly mounted to the crankshaft (e.g., to the main rotary shaft 44) at one side of the crank throw for rotation with the crankshaft about the rotational axis. A flywheel 58 is rigidly mounted to the crankshaft (e.g., to the main rotary shaft 46) to an opposite side of the crank throw for rotation with the crankshaft about the rotational axis.

In the illustrated embodiment, the flywheels 56 and 58 are configured with openings 60 to receive inserts 62 that can be used to vary the flywheel weight.

A drive motor 64 effects rotation of both flywheel 56 and flywheel 58 in order to rotate the crankshaft. The drive motor 64 is operatively coupled to the flywheel 56 via a drive link 66 located to the one side of the crank throw and the drive motor 64 is operatively coupled to the flywheel 58 via a drive link 68 located to the opposite side of the crank throw. In the illustrated embodiment, the drive motor 64 is coupled by a pulley and belt arrangement 67 to effect rotation of an input drive shaft 70 that extends substantially parallel to the rotational axis of the crankshaft. The drive links 66 and 68 are formed by respective belt linkages 72 and 74 extending between spaced apart pulleys 76 and 78 on the input drive shaft and the flywheels 56 and 58. The input drive shaft is mounted below the first and second flywheels and extends between supports 80 and 82 mounted to the support frame 54. The belt linkages 72 and 74 peripherally engage the respective flywheels 56 and 58 in order to drive them.

The crank throw counterweights 48 and 50 are located to opposite sides of the crank throw and are located intermediate the crank throw and respective flywheels 56 and 58. The crank throws counterweights 48 and 50 are configured such that each has center of gravity positioned diametrically opposite the crank throw about the rotational axis of the crankshaft. The flywheels 56 and 58 are symmetrically positioned relative to and on opposite sides of the crank throw and are substantially the same in size and weight (e.g., where the flywheels is configured to accept inserts, similar inserts would be used in each flywheel). The crank throw counterweights 48 and 50 are also symmetrically positioned relative to and on opposite sides of the crank throw and are substantially the same size and weight. This arrangement provides a balanced dual flywheel drive system that helps reduce the required torque needed to accelerate and decelerate the product load in the retort compared to a conventional direct driven shaft and motor/gear reducer. The utilization of dual flywheels reduces the motor horsepower required to accelerate and decelerate a weight load (e.g., at a range 600-2000 pounds) moving in a range of stroke (e.g., 1" to 12") at accelerations ranging from 0 to 2 g. The rotational energy produced by the motor is transformed to linear reciprocating motion using the dual flywheel and crank design.

Figure 3:
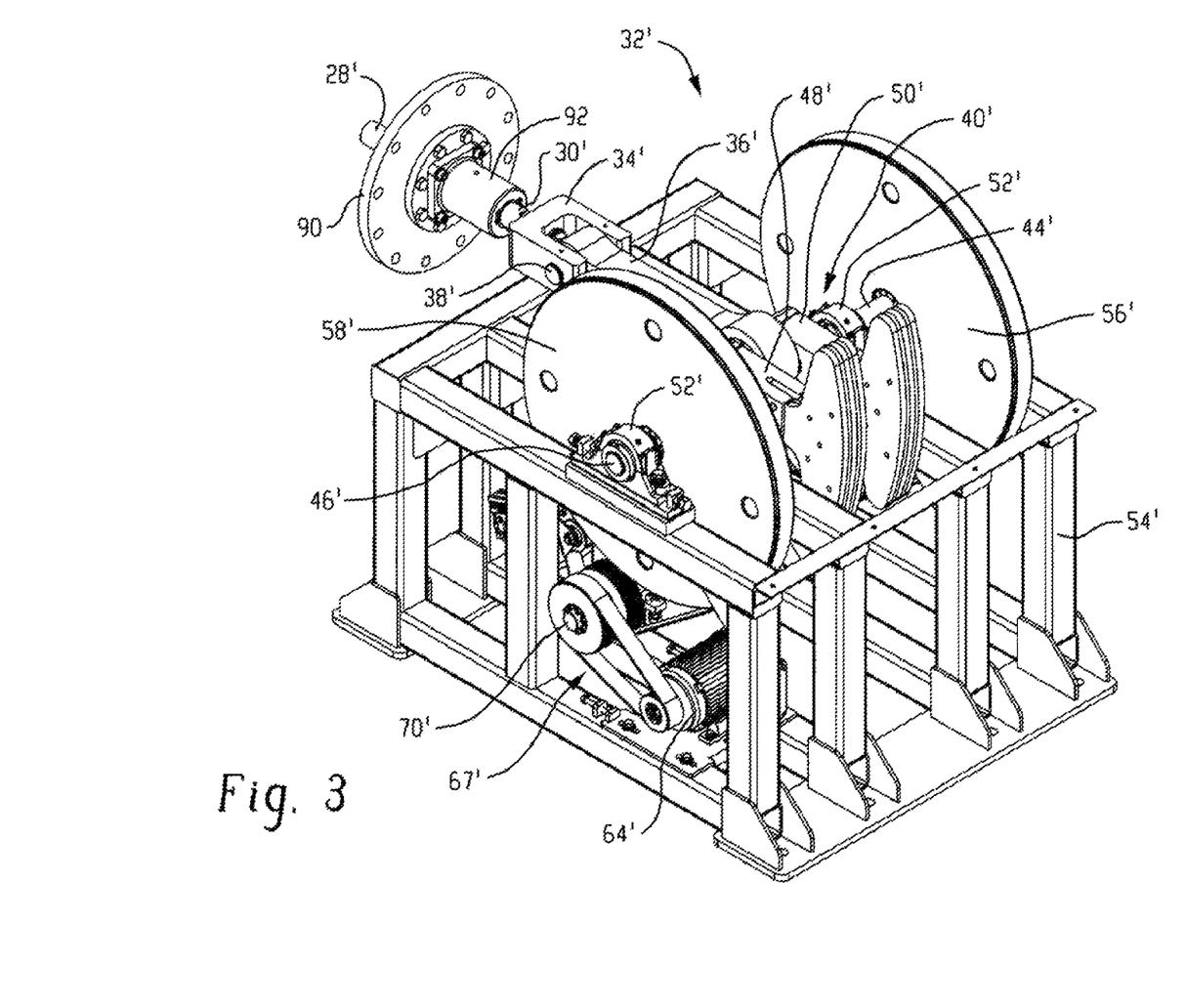
FIG. 3 is a perspective view of an alternative retort system drive arrangement.
Figure 4:
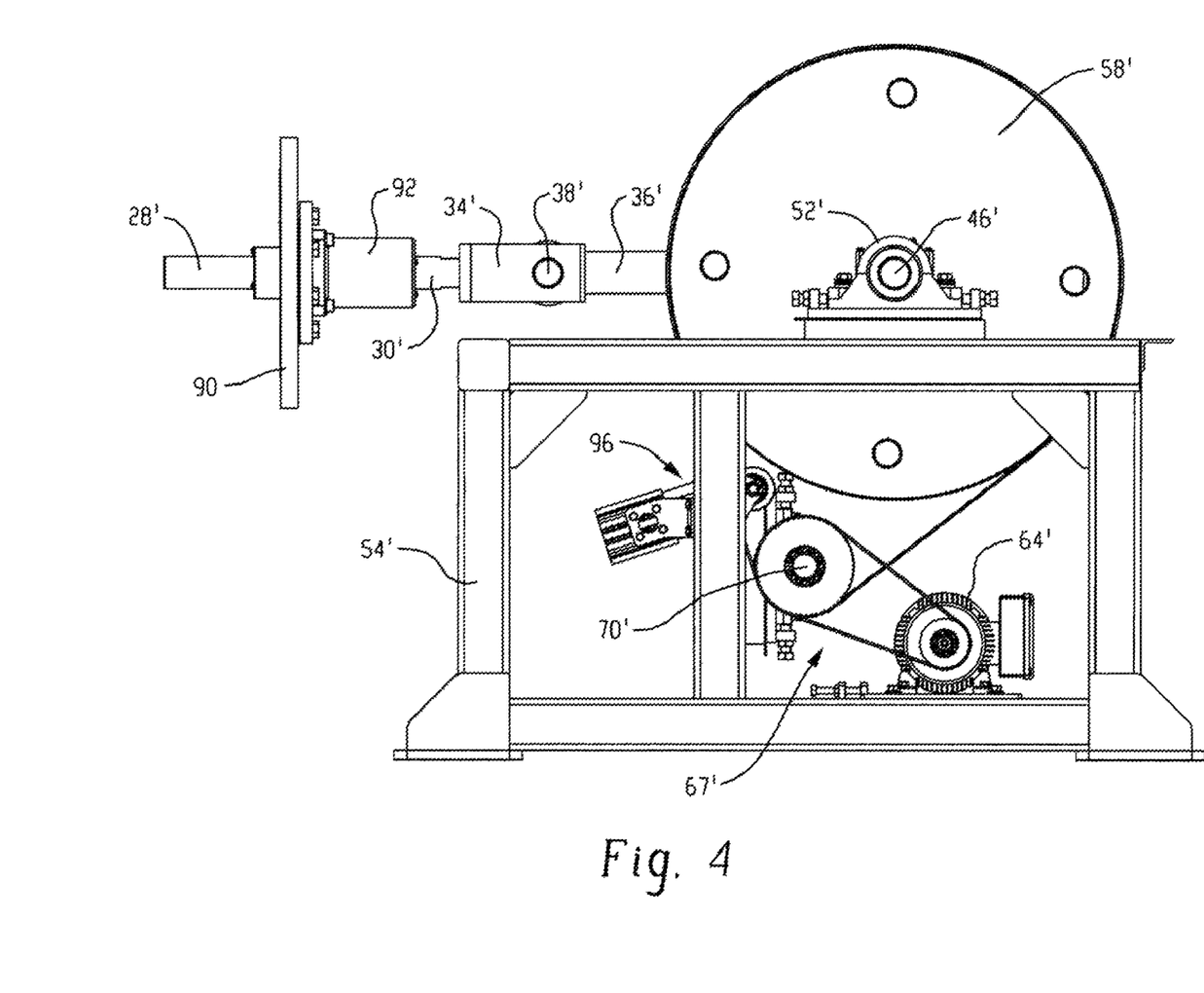
FIG. 4 is a side elevation of the drive arrangement of FIG. 3.
Figure 5:
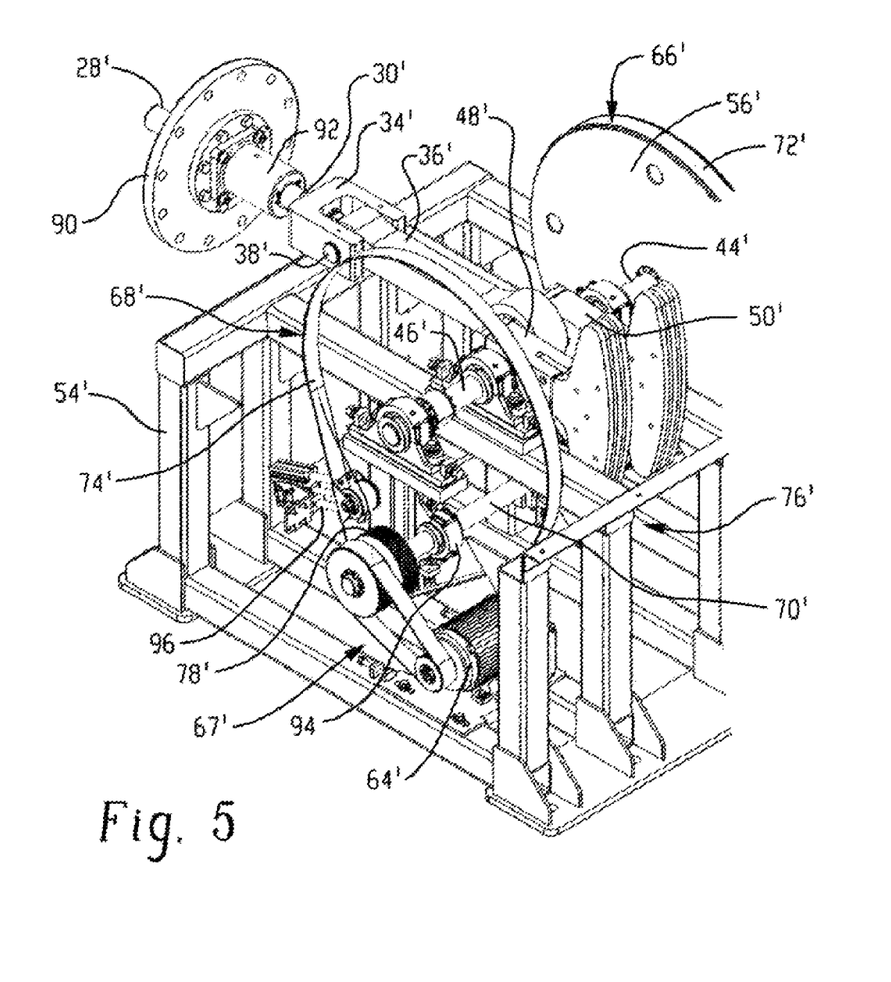
FIG. 5 is a partial perspective view of the drive arrangement of FIG. 3 with certain components removed.

Referring now to FIGS. 3-5, an alternative embodiment of a drive arrangement 32' for a retort system is shown. Internal arm end 28' and external arm end 30' are shown passing through a vessel flange 90 that, when attached to the retort vessel (not shown) becomes part of the vessel wall. A sealed, pressed bearing housing 92, through which the product agitating arm also extends, is mounted to the exterior of the vessel flange 90. Similar to drive arrangement 32, in this embodiment the arm end 30' is coupled to a female clevis 34' that is, in turn, pivotally connected one end of a connecting rod 36' via clevis pin 38'. The opposite end of the connecting rod 36' is pivotally connected to a crank throw of a crankshaft 40', where the rotational axis of the crankshaft is offset from the crank throw. The crankshaft is formed of multiple components including axially aligned main rotary shafts 44' and 46' that are rigidly connected to respective crank throw counterweights 48' and 50', which are in turn rigidly connected to a shaft forming the crank throw. Each of the main rotary shafts 44' and 46' is supported by a respective pair of spaced apart bearing blocks 52', which are mounted to a support frame 54'. A flywheel 56' is rigidly mounted to the crankshaft (e.g., to the main rotary shaft 44') at one side of the crank throw for rotation with the crankshaft about the rotational axis. Another flywheel 58' is rigidly mounted to the crankshaft (e.g., to the main rotary shaft 46') to an opposite side of the crank throw for rotation with the crankshaft about the rotational axis.

A drive motor 64' effects rotation of both flywheel 56' and flywheel 58' in order to rotate the crankshaft. The drive motor 64' is operatively coupled to the flywheel 56' via a drive link 66' located to the one side of the crank throw and the drive motor 64' is operatively coupled to the flywheel 58' via a drive link 68' located to the opposite side of the crank throw. In the illustrated embodiment, the drive motor 64' is coupled by a pulley and belt arrangement 67' to effect rotation of an input drive shaft 70' that extends substantially parallel to the rotational axis of the crankshaft. The drive links 66' and 68' are formed by respective belt linkages 72' and 74' extending between spaced apart pulleys 76' and 78' on the input drive shaft and the flywheels 56' and 58'. The input drive shaft is mounted below the first and second flywheels using spaced apart bearing blocks 94 mounted to the support frame 54'. The belt linkages 72' and 74' peripherally engage the respective flywheels 56' and 58' in order to drive them. Each belt linkage 72' and 74' includes a respective belt tensioner arrangement 96.

The crank throw counterweights 48' and 50' are located to opposite sides of the crank throw and are located intermediate the crank throw and respective flywheels 56' and 58'. The crank throws counterweights 48' and 50' are configured such that each has center of gravity positioned diametrically opposite the crank throw about the rotational axis of the crankshaft. The flywheels 56' and 58' are symmetrically positioned relative to and on opposite sides of the crank throw and are substantially the same in size and weight, and the crank throw counterweights 48' and 50' are also symmetrically positioned relative to and on opposite sides of the crank throw and are substantially the same size and weight. Again, this arrangement provides a balanced dual flywheel drive system that helps reduce the required torque needed to accelerate and decelerate the product load in the retort compared to a conventional direct driven shaft and motor/gear reducer.

Figure 6:
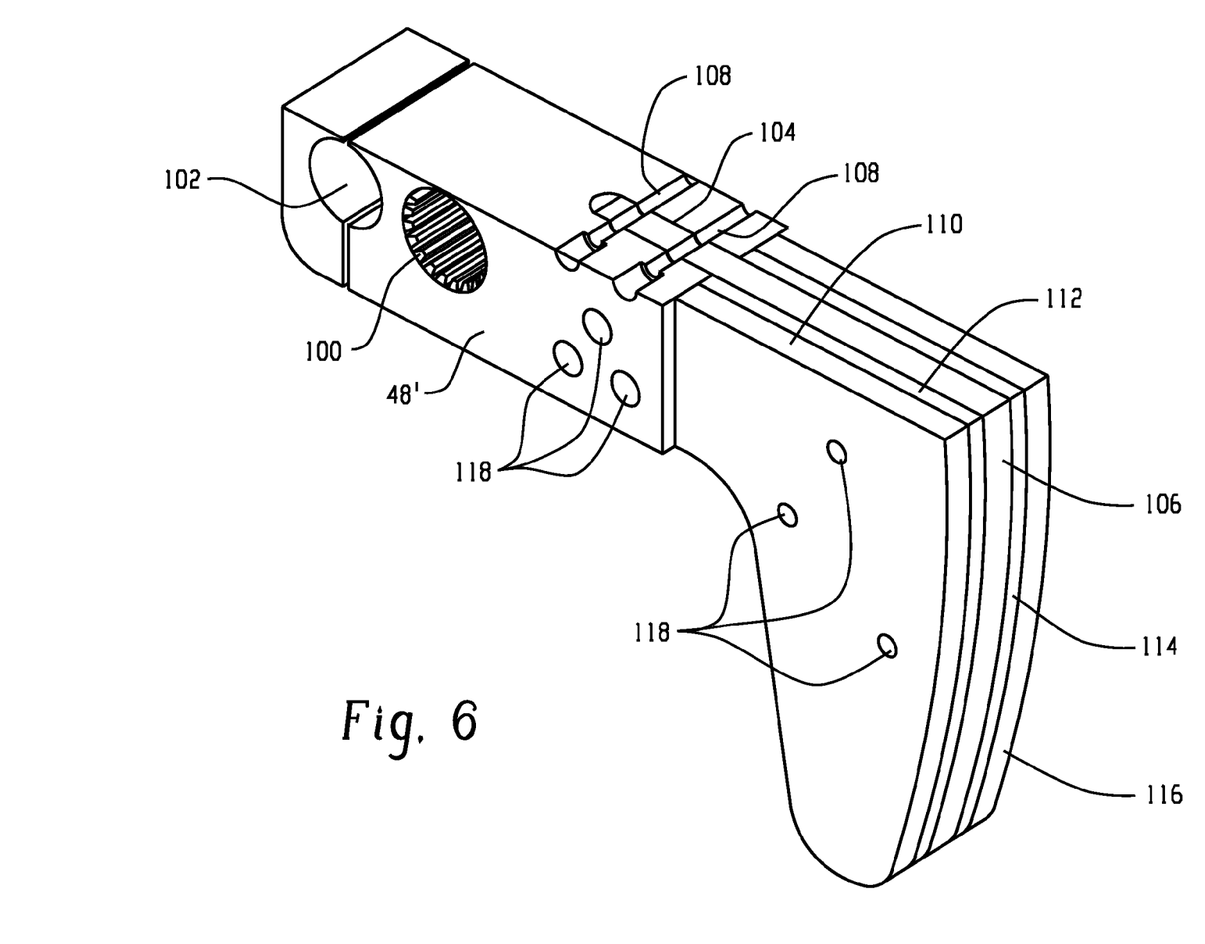
FIG. 6 is a cross-section of one embodiment of a crank throw counterweight structure.

The crank throw counterweights 48' and 50' are adapted for varying the weight of the counterweights in accordance with the product load to be driven by the drive arrangement. Specifically, and as best seen in the cross-section of counterweight 48' shown in FIG. 6. Toothed opening 100 is provided to receive a mating end of the main rotary shaft 44' (not shown) so that rotation of the main rotary shaft will effect rotation of the counterweight arm. Opening 102 is provided to receive one end of the crank throw (not shown). The end of the counterweight arm opposite the crank throw is adapted to receive a plurality of plates that can be varied to adjust the weight of the counterweight. Specifically, a spline or groove 104 is provided to receive the end of a primary plate structure 106 that is secured via bolts passing through holes 108. The primary plate 106 forms the base structure for attaching a series of additional plates 110, 112, 114, 116 on either side of the primary plate 106 via fasteners that pass through aligned openings 118 on the plates. Utilizing this structure, a method of constructing a retort system that is adapted for movement of the product load involves, determining a product load to be moved by operation of the drive arrangement. Dependent upon the product load, desired weights are defined for crank throw counterweight structures (e.g., based upon prior testing and/or calculations) and a suitable number of plate structures may be attached to the primary plate 106 to achieve the desired weight for the counterweights.

Figure 7:
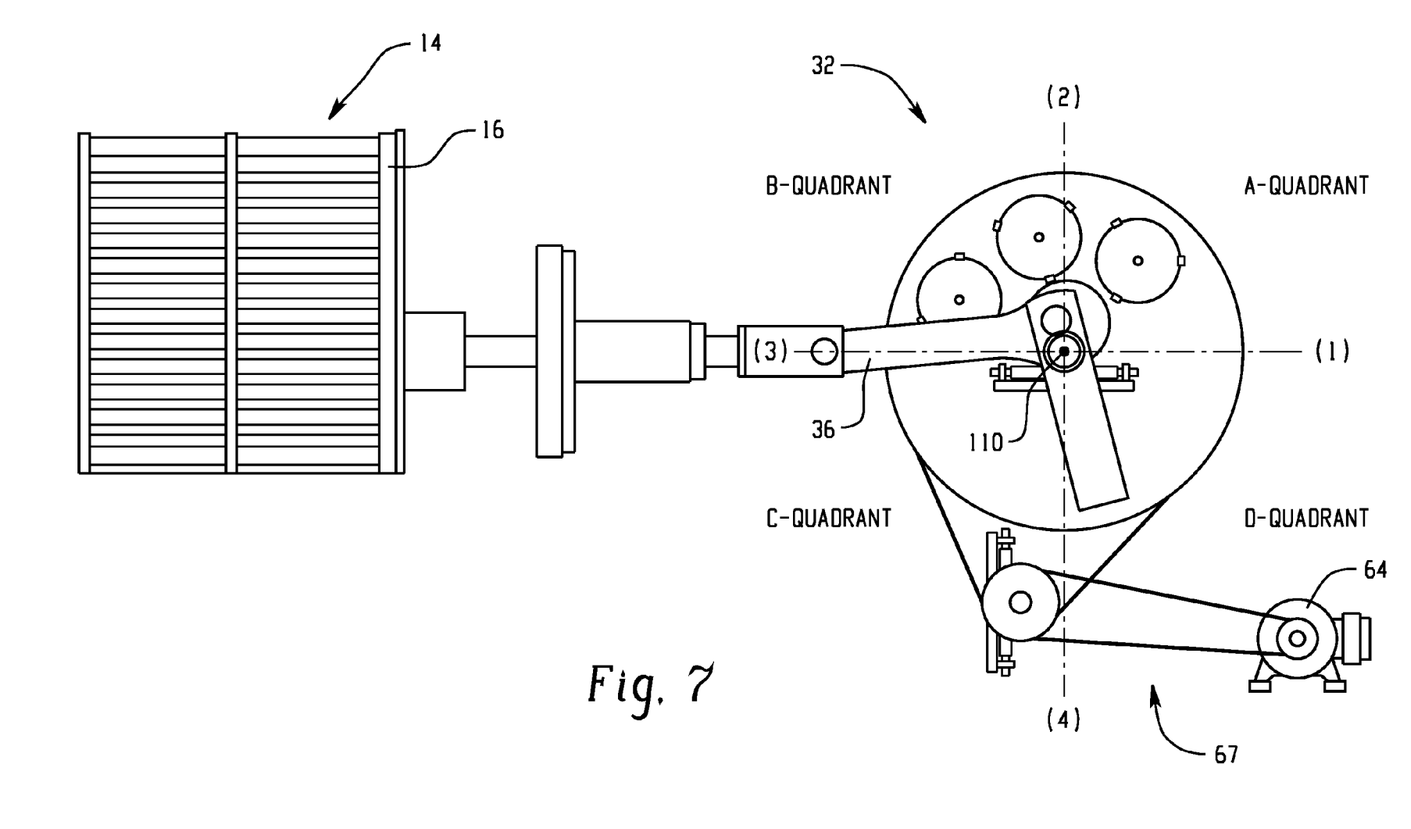
FIG. 7 is a partial side elevation view the retort system of FIG. 1 showing quadrants of movement for the crank throw.

An understanding of the operation of the above drive arrangements can be made with reference to FIG. 7, showing drive arrangement 32. The rotational axis of the system crankshaft is shown at 110, with the pivotal connection between the crank arm 42 and connecting rod 36 offset therefrom. Four quadrants of possible crank throw positions are shown as quadrants A, B, C and D. The position shown has the crank throw in the beginning of quadrant B slightly past point 2. During normal running of the device in a counterclockwise direction, the motor 64 initially stores energy into the flywheel system. This stored energy as well as the motor supplied energy is used to accelerate the reciprocating mass from stopped to full speed (e.g., when the crank throw move circumferentially from point 1 to point 2 through quadrant A the product 14 within the vessel is accelerated). This energy expended to accelerate the product mass would slightly slow down or decelerate the flywheels (i.e. the flywheels give up energy to the moving reciprocating mass). This trading of energy also occurs in quadrant C (e.g., when the crank throw moves circumferentially from points 3 to 4) except in the opposite direction of product travel. As the crank throw moves through quadrant B from point 2 to point 3, the product must come to a complete stop in order to reverse direction, and once more the it's kinetic energy is transferred back to the flywheels, but now causing the flywheels to slightly speed up. Thus, the energy expended by the system during the product load acceleration that occurs during crank throw movement through quadrants A and C is re-gained during the product load deceleration that occurs during crank throw movement through quadrants B and D respectively. Once the drive arrangement is moving at speed, the motor is only required to make up slight losses caused by bearing friction and packing drag, therefore requiring significantly less torque than a direct drive system.

Notably, the drive arrangement support structures 54 and 54' are independent from both the vessel and the vessel support structure (e.g., base structure 130 shown in FIG. 1). This arrangement reduces stress applied to the vessel structure, with the substantial majority of the stress being taken by the support frame structures 54 and 54', which can, for example, be bolted or otherwise secured to the floor at the site of retort system operation.

It is to be clearly understood that the above description is intended by way of illustration and example only and is not intended to be taken by way of limitation, and that changes and modifications are possible. For example, while a multi-component crankshaft is described above, it is recognized that, in some embodiments, the crankshaft could be formed as a unitary piece (e.g., a unitary forging or machined from a single piece of material). Moreover, while each of the flywheels is shown as being driven by belts that peripherally engage the flywheels, other drive links for the flywheels could be provided (e.g., the flywheels could be formed as toothed flywheels that directly engaged toothed gears mounted on the input drive shaft). Other variations are possible.

What is claimed is:

1. A retort system, comprising:
a vessel defining a heating chamber and including a product receiving area therein;
a product agitating arm mounted for reciprocating movement through a wall of the vessel and having a first end within the vessel and a second end outside the vessel;
a drive arrangement exterior of the vessel and operatively coupled to the arm for moving the arm in a reciprocating manner, the drive arrangement including:
   a crankshaft assembly including a crank throw operatively coupled to the arm, the crankshaft assembly having a rotational axis offset from the crank throw;
   a first flywheel mounted to the crankshaft assembly to a first side of the crank throw for rotation with the crankshaft assembly about the rotational axis; and
   a second flywheel mounted to the crankshaft assembly to a second side of the crank throw for rotation with the crankshaft assembly about the rotational axis;
the drive arrangement further includes:
   a drive motor for effecting rotation of the first flywheel and the second flywheel, the drive motor operatively coupled to the first flywheel via a first drive link located to the first side of the crank throw and the drive motor operatively coupled to the second flywheel via a second drive link located to the second side of the crank throw;
wherein:
   the drive motor effects rotation of an input drive shaft that extends substantially parallel to the rotational axis of the crankshaft;
   the first drive link is a first belt linkage between a first pulley on the input drive shaft and the first flywheel; and
   the second drive link is a second belt linkage between a second pulley on the input drive shaft and the second flywheel.

2. The retort system of claim 1, wherein:
the input drive shaft is mounted below the first and second flywheels;
the first belt linkage peripherally engages the first flywheel; and
the second belt linkage peripherally engages the second flywheel.

3. A retort system, comprising:
a vessel defining a heating chamber and including a product receiving area therein;
a product agitating arm mounted for reciprocating movement through a wall of the vessel and having a first end within the vessel and a second end outside the vessel;
a drive arrangement exterior of the vessel and operatively coupled to the arm for moving the arm in a reciprocating manner, the drive arrangement including:
   a crankshaft assembly including a crank throw operatively coupled to the arm, the crankshaft assembly having a rotational axis offset from the crank throw;
   a first flywheel mounted to the crankshaft assembly to a first side of the crank throw for rotation with the crankshaft assembly about the rotational axis;
   a second flywheel mounted to the crankshaft assembly to a second side of the crank throw for rotation with the crankshaft assembly about the rotational axis; and
the drive arrangement further includes:
   a first crank throw counterweight located to the first side of the crank throw and intermediate the crank throw and the first flywheel; and
   a second crank throw counterweight located to the second side of the crank throw and intermediate the crank throw and the second flywheel.

4. The retort system of claim 3, wherein:
the first crank throw counterweight has a center of gravity positioned diametrically opposite the crank throw about the rotational axis of the crankshaft assembly; and
the second crank throw counterweight has a center of gravity positioned diametrically opposite the crank throw about the rotational axis of the crankshaft assembly.

5. The retort system of claim 4, wherein:
the first crank throw counterweight comprises a first primary plate connected to the crankshaft assembly and one or more plate structures removably attached to the first primary plate to facilitate varying the weight of the first crank throw counterweight; and
the second crank throw counterweight comprises a second primary plate connected to the crankshaft assembly and one or more plate structures removably attached to the second primary plate to facilitate varying the weight of the second crank throw counterweight.

6. The retort system of claim 4, wherein:
the first flywheel and second flywheel are symmetrically positioned relative to the crank throw and are substantially the same in size and weight; and
the first crank throw counterweight and second crank throw counterweight are symmetrically positioned relative to the crank throw and are substantially the same size and weight.

7. A retort system, comprising:
a vessel defining a heating chamber and including a product receiving area therein;
a product agitating arm mounted for reciprocating movement through a wall of the vessel and having a first end within the vessel and a second end outside the vessel;
a drive arrangement exterior of the vessel and operatively coupled to the arm for moving the arm in a reciprocating manner, the drive arrangement including:
   a crankshaft assembly including a crank throw operatively coupled to the arm the crankshaft assembly having a rotational axis offset from the crank throw;
   a first flywheel mounted to the crankshaft assembly to a first side of the crank throw for rotation with the crankshaft assembly about the rotational axis;
   a second flywheel mounted to the crankshaft assembly to a second side of the crank throw for rotation with the crankshaft assembly about the rotational axis; and
the drive arrangement includes a support structure that is independent of both the vessel and a support structure of the vessel.

8. A retort system, comprising:
a vessel defining a heating chamber and including a product receiving area therein;
a product agitating arm mounted for reciprocating movement through a wall of the vessel and having a first end within the vessel and a second end outside the vessel;
a drive arrangement exterior of the vessel and operatively coupled to the arm for moving the arm in a reciprocating manner, the drive arrangement including:
   a crankshaft assembly including a crank throw operatively coupled to the arm, the crankshaft assembly having a rotational axis offset from the crank throw;
   a first flywheel mounted to the crankshaft assembly to a first side of the crank throw for rotation with the crankshaft assembly about the rotational axis;

a second flywheel mounted to the crankshaft assembly to a second side of the crank throw for rotation with the crankshaft assembly about the rotational axis; and the first flywheel is configured with one or more removable inserts to facilitate varying weight of the first flywheel; and the second flywheel is configured with one or more removable inserts to facilitate varying weight of the second flywheel.

9. A method of constructing a retort system, comprising: providing a retort system that includes:
- a vessel defining a heating chamber and including a product receiving area therein;
- a product agitating arm mounted for reciprocating movement through a wall of the vessel and having a first end within the vessel and a second end outside the vessel;
- a drive arrangement exterior of the vessel and operatively coupled to the arm for moving the arm in a reciprocating manner, the drive arrangement including:
  - a crankshaft assembly including a crank throw operatively coupled to the arm, the crankshaft assembly having a rotational axis offset from the crank throw;
  - a first flywheel mounted to the crankshaft assembly to a first side of the crank throw for rotation with the crankshaft assembly about the rotational axis;
  - a second flywheel mounted to the crankshaft assembly to a second side of the crank throw for rotation with the crankshaft assembly about the rotational axis; and determining a product load to be moved by operation of the drive arrangement;

dependent upon the product load, defining a first weight for a first crank throw counterweight structure and a second weight for a second crank throw counterweight structure;

providing a first crank throw counterweight to the first side of the crank throw and intermediate the crank throw and the first flywheel, the first crank throw counterweight having the first weight; and providing a second crank throw counterweight to the second side of the crank throw and intermediate the crank throw and the second flywheel, the second crank throw counterweight having the second weight.

* * * * *